(12) United States Patent
Merianos et al.

(10) Patent No.: US 7,935,732 B2
(45) Date of Patent: May 3, 2011

(54) ANTIMICROBIAL COMPOSITIONS

(75) Inventors: John J. Merianos, Middletown, NJ (US); Paul Garelick, South Plainfield, NJ (US); Susan M. Lindstrom, Ramsey, NJ (US)

(73) Assignee: ISP Investments Inc., Wilmington, DE (US)

( * ) Notice: Subject to any disclaimer, the term of this patent is extended or adjusted under 35 U.S.C. 154(b) by 1781 days.

(21) Appl. No.: 10/820,349

(22) Filed: Apr. 8, 2004

(65) Prior Publication Data

US 2005/0228032 A1    Oct. 13, 2005

(51) Int. Cl.
*A01N 31/00* (2006.01)

(52) U.S. Cl. ..................................................... 514/738

(58) Field of Classification Search ............... 514/375, 514/479, 769, 772, 772.4, 789, 738
See application file for complete search history.

(56) References Cited

U.S. PATENT DOCUMENTS

| | | | | |
|---|---|---|---|---|
| 5,428,050 A | * | 6/1995 | Merianos | 514/390 |
| 5,516,510 A | * | 5/1996 | Beilfuss et al. | 424/65 |
| 5,733,362 A | * | 3/1998 | Hahn | 106/18.33 |
| 6,607,738 B2 | * | 8/2003 | Salmon et al. | 424/402 |
| 7,115,641 B2 | * | 10/2006 | Merianos et al. | 514/375 |
| 7,582,681 B2 | * | 9/2009 | Schmaus et al. | 514/738 |

FOREIGN PATENT DOCUMENTS

| | | | |
|---|---|---|---|
| DE | 10206759 A1 | * | 8/2003 |
| EP | 1206933 A1 | * | 5/2002 |
| EP | 1238651 A1 | * | 9/2002 |
| JP | 11322591 A | * | 11/1999 |
| JP | 2003286153 A | * | 10/2003 |

OTHER PUBLICATIONS

Windholz et al., The Merck Index, 10th Edition, pp. 1247-1248, abstract No. 8567 (1983).*
Ingredients—Sorbic acid, http://sci-toys.com/ingredients/sorbic_acid.html.*

* cited by examiner

*Primary Examiner* — Kevin Weddington
(74) *Attorney, Agent, or Firm* — William J. Davis; Thompson Hine LLP

(57) ABSTRACT

What is described herein are antimicrobial compositions which are defined blends of a 1,2-diol and phenoxyethanol which show broad activity against bacteria, fungi and mold spores. This activity is potentiated by the addition thereto of small amounts of a co-biocide for which the blend acts as a delivery system for the otherwise water-insoluble co-biocide.

6 Claims, No Drawings

ANTIMICROBIAL COMPOSITIONS

BACKGROUND OF THE INVENTION

1. Field of the Invention

This invention relates to antimicrobial compositions, and, more particularly, to a defined blend of a 1,2-diol and phenoxyethanol, optionally with a co-biocide, which compositions show broad activity against bacteria, fungi and mold spores.

2. Description of the Prior Art

Personal care products come in many different forms. They include creams, lotions, pastes, liquids, aerosols, shampoos, gels, wipes, bats, sticks, powders and granules any or all of which are intended for topical application to the skin including the scalp and the mucosa including the lips.

The products are generally designed to have a substantial shelf life. The products need to be manufactured at one site, transported possibly over a considerable distance to a depot or other storage facility prior to further transport to a point of sale. The product may then spend considerable time on a retailer's shelf prior to purchase and further storage by the user whether for individual use or use in, for example, a hotel, workplace, institution or the like. All of such storage will take place under uncontrolled conditions including considerable variation in temperature.

In order to keep bacterial and fungal growth in such products at an acceptable level it is conventional practice for the products to contain a preservative. Many preservatives are available. The appropriate preservative has to be selected with regard to its efficacy and its acceptability to contact with human or animal skin. With regard to its acceptability there are in many countries laws and regulations governing the maximum permitted content of preservative in products intended for human use due to their possible toxic or otherwise harmful effect.

The need to control microbiological growth in personal care products is known to be particularly acute in water based products such as non-ionic oil-in-water emulsions and in pre-impregnated wipes such as baby wipes.

For example, U.S. Pat. No. 6,607,738 described a preservative system of iodopropynyl butyl carbamate (IPBC) and phenoxyethanol (PE) in a weight ratio of 1:90 to 1:400 for use in personal care products.

U.S. Pat. No. 5,516,510 also disclosed deodorizing active ingredients to reduce the unpleasant odor caused by microorganisms which comprised a glycerin monoalkyl ether in combination with an astringent and/or a naturally occurring deodorant.

EP 1206933 described a preservative composition of caprlyl glycol (1,2-octanediol) and iodopropynyl butyl carbamate in a weight ratio of 0.1 to 500.

U.S. Pat. No. 5,733,362 was directed to a bacterial composition of 2-methyl-4,5-trimethylene-4-isothiazoline-3-on; 3-iodo-2-propynyl butyl carbamate and 2-phenoxyethanol.

EP 1238651 described that the activity of preservative mixtures of iodopropynyl butyl carbamate and phenoxyethanol, in a weight ratio of 1:90 to 1:200, preferably 1:100, can be potentiated by adding caprylyl glycol thereto, in a weight ratio of the latter to the mixture of 0.1 to 500, preferably 1:55. Thus the formulation of caprylyl glycol, iodopropynyl butyl carbamate and phenoxyethanol had weight ratios of each of 55:1:100 to 200:1:400, respectively. The personal care formulations contained 0.1-30% caprylyl glycol, preferably 0.5%; with 0.001-1% IPBC, preferably 0.001-0.01%; and with phenoxyethanol of 0.1-3%, preferably 0.5-1%.

JP Application No. 11045504 described an antiseptic microbicide and compositions thereof which contained a 1,2-alkane diol. These compositions effectively reduced the required dosage of conventional antiseptic microbicides such as paraben, benzoic acid and the like. The 1,2-alkane diol therein could be blended with a photosensitizer, benzoic acid or its salt, phenoxyethanol or 4-isopropyl-3-methylphenol. However, there was no disclosure of suitable blends of 1,2-alkane diol and phenoxyethanol at predetermined weight ratios and HLB values, which could deliver water insoluble biocides such as IPBC into aqueous personal care systems at a relatively high concentration of such biocides.

These and other prior art references in this field were concerned with the problem that many are antibacterials such as IPBC have limited aqueous solubility inpersonal care systems; particularly at the high concentrations necessary for effective antimicrobial activity. Thus, at very low concentrations they remain in solution but do not contribute as much activity as desired for these products.

Accordingly, it is desired to provide a blend of 1,2-diol and phenoxyethanol at a predetermined ratio and HLB value which can deliver water insoluble biocides into an aqueous personal care system at relatively high concentrations thereby providing more effective preservative activity in such systems.

SUMMARY OF THE INVENTION

What is described herein is an antimicrobial composition which is active against bacteria, yeast and mold spores, consisting essentially of, by wt.

(a) 40-60% of a 1,2-diol selected from the group consisting of 1,2-pentanediol, 1,2-hexanediol and 1,2-octanediol;

(b) 40-60% of phenoxyethanol; and (c) 0-10% of a co-biocide selected from the group consisting of sorbic acid, benzoic acid, dibromodicyanobutane, iodopropynyl butyl carbamate and 1,2-benzisothiazolin-3-one.

A preferred antimicrobial composition of the invention includes (c) sorbic acid and/or 1% iodopropynyl butyl carbamate.

Most preferred antimicrobial compositions herein are those wherein (a) is about 44% and (b) is about 56%.

Also preferred are antimicrobial compositions wherein (c) is sorbic acid present in an amount of about 5-7% of the composition, or IPBC present in an amount of 1.25-1.50%.

Preferred antimicrobial compositions of the invention include those wherein (a) is 41-42%, (b) is 52-53%; and (c) is sorbic acid 5-7%; and (a) is 43.3; (b) is 55.3; and (c) is IPBC 1.4%.

The invention also encompasses personal care products which include the antimicrobial composition described above, preferably wherein the antibacterial composition is present in an amount of 0.1-2% by weight of the product, most preferably 0.5-1.5%.

DETAILED DESCRIPTION OF THE INVENTION

In accordance with the invention, there is provided herein an antimicrobial composition which is active against bacteria, yeast and mold spores, consisting essentially of, by wt.

(a) 40-60% of a 1,2-diol selected from the group consisting of 1,2-pentanediol, 1,2-hexanediol and 1,2-octanediol;

(b) 40-60% of phenoxyethanol; and (c) 0-10% of a co-biocide selected from the group consisting of sorbic acid, benzoic acid, dibromodicyanobutane, iodopropynyl butyl carbamate and 1,2-benzisothiazolin-3-one.

Preferably the antimicrobial composition includes (c) sorbic acid and/or 1% iodopropynyl butyl carbamate.

Most preferably, the antimicrobial composition includes (a) about 44% and (b) about 56%, and, optionally, (c) is sorbic acid, present in an amount of about 5-7% of the composition, or (c) is IPBC present in an amount of 1.25-1.50%.

Most preferably, it is an antimicrobial composition wherein (a) is 41-42%, (b) is 52-53%; and (c) is sorbic acid 5-7%; most preferably, wherein (a) is 43.3; (b) is 55.3; and (c) is IPBC 1.4%.

Personal care products particularly utilize the antimicrobial composition, preferably, wherein the antibacterial composition is present in an amount of 0.1-2% by weight of the product, most preferably, 0.5-1.5%.

The invention will now be described in more detail by the following challenge test examples on the invention formulations.

EXAMPLE 1

ANTIMICROBIAL: 1,2-Octanediol/Phenoxyethanol (40/60 wt. ratio)
PRODUCT BASE: Screening emulsion (Standard Emulsion)

| TEST ORGANISMS | INOCULUM (0 hours) | REINOCULUM (21 days) |
|---|---|---|
| Staph aureus 6538 | $1.9 \times 10^6$ cfu/ml | $1.2 \times 10^6$ cfu/ml |
| E. coli 8739 | $4.6 \times 10^6$ cfu/ml | $2.1 \times 10^6$ cfu/ml |
| P. aeruginosa 9027 | $1.7 \times 10^6$ cfu/ml | $2.1 \times 10^6$ cfu/ml |
| B. cepacia 25416 | $2.5 \times 10^6$ cfu/ml | $2.0 \times 10^6$ cfu/ml |
| C. albicans 10231 | $2.7 \times 10^6$ cfu/ml | $9.0 \times 10^5$ cfu/ml |
| A. niger 16404 | $3.0 \times 10^5$ cfu/ml | $1.0 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.5% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 2.2E5 | <10 | <10 | <10 | <10 |
| A. niger 16404 | 5.5E5 | 2E4 | 3.8E2 | 6E1 | 6.6E3 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 1.4E5 | <10 | <10 | <10 | <10 |

EXAMPLE 2

ANTIMICROBIAL: 1,2-Octanediol/Phenoxyethanol (40/60)
PRODUCT BASE: Nonionic emulsion

| TEST ORGANISMS | INOCULUM (0 hours) | REINOCULUM (21 days) |
|---|---|---|
| Staph aureus 6538 | $1.3 \times 10^6$ cfu/ml | $8.0 \times 10^6$ cfu/ml |
| E. coli 8739 | $3.9 \times 10^6$ cfu/ml | $4.8 \times 10^6$ cfu/ml |
| P. aeruginosa 9027 | $2.5 \times 10^6$ cfu/ml | $4.7 \times 10^6$ cfu/ml |
| B. cepacia 25416 | $1.5 \times 10^6$ cfu/ml | $1.0 \times 10^6$ cfu/ml |
| C. albicans 10231 | $3.2 \times 10^6$ cfu/ml | $1.6 \times 10^6$ cfu/ml |
| A. niger 16404 | $4.0 \times 10^5$ cfu/ml | $2.6 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.5% | | | | | |
| Staph. aureus 6538 | 1.4E5 | <10 | <10 | <10 | <10 |
| E. coli 8739 | 6.6E3 | <10 | <10 | <10 | <10 |
| P. aeruginosa 9027 | <10 | <10 | <10 | <10 | <10 |
| B. cepacia 25416 | 4.0E4 | <10 | <10 | <10 | <10 |
| C. albicans 10231 | >1E6 | 8.1E5 | 5.2E4 | <10 | >1E4 |
| A. niger 16404 | 5.9E5 | 1.9E5 | 3.5E4 | 1.2E4 | 6.9E5 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 3.4E5 | <10 | <10 | <10 | <10 |
| A. niger 16404 | 6.5E5 | 2.4E4 | 1.2E3 | 9E1 | >1E4 |

EXAMPLE 3

ANTIMICROBIAL: 1,2-Octanediol/Phenoxyethanol (40/60)/1.5% BIT
PRODUCT BASE: Screening Emulsion

| TEST ORGANISMS | INOCULUM (0 hours) | REINOCULUM (21 days) |
|---|---|---|
| Staph aureus 6538 | $4.9 \times 10^6$ cfu/ml | $2.6 \times 10^6$ cfu/ml |
| E. coli 8739 | $5.6 \times 10^6$ cfu/ml | $4.3 \times 10^6$ cfu/ml |
| P. aeruginosa 9027 | $3.1 \times 10^6$ cfu/ml | $3.2 \times 10^6$ cfu/ml |
| B. cepacia 25416 | $2.7 \times 10^6$ cfu/ml | $1.8 \times 10^6$ cfu/ml |
| C. albicans 10231 | $4.2 \times 10^6$ cfu/ml | $1.7 \times 10^7$ cfu/ml |
| A. niger 16404 | $1.9 \times 10^5$ cfu/ml | $4.0 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.67% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |
| USE LEVEL: 1.33% (200 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

EXAMPLE 4

ANTIMICROBIAL: 1,2-Octanediol/Phenoxyethanol (40/60)/1.5% BIT
PRODUCT BASE: Nonionic Emulsion

| TEST ORGANISMS | INOCULUM (0 hours) | REINOCULUM (21 days) |
|---|---|---|
| Staph aureus 6538 | $1.2 \times 10^6$ cfu/ml | $3.7 \times 10^6$ cfu/ml |
| E. coli 8739 | $3.2 \times 10^6$ cfu/ml | $3.1 \times 10^6$ cfu/ml |
| P. aeruginosa 9027 | $3.0 \times 10^6$ cfu/ml | $4.6 \times 10^6$ cfu/ml |
| B. cepacia 25416 | $6.0 \times 10^5$ cfu/ml | $3.2 \times 10^6$ cfu/ml |
| C. albicans 10231 | $2.8 \times 10^6$ cfu/ml | $2.4 \times 10^6$ cfu/mml |
| A. niger 16404 | $7.0 \times 10^5$ cfu/ml | $4.0 \times 10^5$ cfu/ml |

| TEST ORGANISMS | 48 HRS | 7 D | 14 D | 21 D | 28 D |
|---|---|---|---|---|---|
| USE LEVEL: 0.67% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 3E1 | <10 | <10 | <10 | <10 |
| USE LEVEL: 1.33% (200 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

EXAMPLE 5

ANTIMICROBIAL: 1,2-Octanediol/Phenoxyethanol (40/60)/1.5% BIT
PRODUCT BASE: Screening Emulsion

| TEST ORGANISMS | INOCULUM (0 hours) | REINOCULUM (21 days) |
|---|---|---|
| Staph aureus 6538 | $3.7 \times 10^6$ cfu/ml | $2.9 \times 10^6$ cfu/ml |
| E. coli 8739 | $3.1 \times 10^6$ cfu/ml | $5.4 \times 10^6$ cfu/ml |
| P. aeruginosa 9027 | $4.6 \times 10^6$ cfu/ml | $3.8 \times 10^6$ cfu/ml |
| B. cepacia 25416 | $3.2 \times 10^6$ cfu/ml | $2.9 \times 10^6$ cfu/ml |
| C. albicans 10231 | $2.4 \times 10^6$ cfu/ml | $2.2 \times 10^6$ cfu/ml |
| A. niger 16404 | $4.0 \times 10^5$ cfu/ml | $2.9 \times 10^5$ cfu/ml |

| TEST ORGANISMS | 48 HRS | 7 D | 14 D | 21 D | 28 D |
|---|---|---|---|---|---|
| USE LEVEL: 0.25% (37.5 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 7.1E2 | <10 | <10 | <10 | <10 |
| A. niger 16404 | 4.2E4 | 3.4E3 | 1.2E2 | 2E1 | 6.7E2 |
| USE LEVEL: 0.5% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | 2E1 (replate <10) |

EXAMPLE 6

ANTIMICROBIAL: 1,2-Octanediol/Phenoxyethanol (40/60)/1.5% BIT
PRODUCT BASE: Nonionic Emulsion

| TEST ORGANISMS | INOCULUM (0 hours) | REINOCULUM (21 days) |
|---|---|---|
| Staph aureus 6538 | $4.9 \times 10^6$ cfu/ml | $4.8 \times 10^6$ cfu/ml |
| E. coli 8739 | $3.5 \times 10^6$ cfu/ml | $3.1 \times 10^6$ cfu/ml |
| P. aeruginosa 9027 | $4.0 \times 10^6$ cfu/ml | $3.0 \times 10^6$ cfu/ml |
| B. cepacia 25416 | $4.0 \times 10^6$ cfu/ml | $2.2 \times 10^6$ cfu/ml |
| C. albicans 10231 | $3.5 \times 10^6$ cfu/ml | $8.0 \times 10^5$ cfu/ml |
| A. niger 16404 | $2.7 \times 10^6$ cfu/ml | $1.8 \times 10^5$ cfu/ml |

| TEST ORGANISMS | 48 HRS | 7 D | 14 D | 21 D | 28 D |
|---|---|---|---|---|---|
| USE LEVEL: 0.25% (37.5 ppm BIT) | | | | | |
| Staph. aureus 6538 | 2E1 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | 2E1 | <10 | <10 | <10 | <10 |
| C. albicans 10231 | >1E6 | 7.2E2 | 1E2 | <10 | >1E4 |
| A. niger 16404 | 3.9E5 | 2.4E5 | 1.9E5 | 1.6E5 | 2.5E5 |
| USE LEVEL: 0.50% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 4.4E4 | 2E3 | 5E1 | <10 | 3.5E3 |

EXAMPLE 7

ANTIMICROBIAL: 1,2-Octanediol/Phenoxyethanol (40/60)/1.5% BIT
PRODUCT BASE: Screening Emulsion

| TEST ORGANISMS | INOCULUM (0 hours) | REINOCULUM (21 days) |
|---|---|---|
| Staph aureus 6538 | $3.6 \times 10^6$ cfu/ml | $2.8 \times 10^6$ cfu/ml |
| E. coli 8739 | $5.8 \times 10^6$ cfu/ml | $3.5 \times 10^6$ cfu/ml |
| P. aeruginosa 9027 | $4.0 \times 10^6$ cfu/ml | $3.2 \times 10^6$ cfu/ml |
| B. cepacia 25416 | $3.0 \times 10^6$ cfu/ml | $1.8 \times 10^6$ cfu/ml |
| C. albicans 10231 | $2.7 \times 10^6$ cfu/ml | $1.7 \times 10^6$ cfu/ml |
| A. niger 16404 | $1.3 \times 10^6$ cfu/ml | $4.9 \times 10^5$ cfu/ml |

| TEST ORGANISMS | 48 HRS | 7 D | 14 D | 21 D | 28 D |
|---|---|---|---|---|---|
| USE LEVEL: 0.50% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

| | USE LEVEL: 0.67% (100 ppm BIT) | | | | |
|---|---|---|---|---|---|
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

EXAMPLE 8

ANTIMICROBIAL: 1,2-Octanediol/Phenoxyethanol (40/60)/2.5% BIT

PRODUCT BASE: Screening Emulsion

| TEST ORGANISMS | INOCULUM (0 hours) | REINOCULUM (21 days) |
|---|---|---|
| Staph aureus 6538 | $3.6 \times 10^6$ cfu/ml | $2.8 \times 10^6$ cfu/ml |
| E. coli 8739 | $5.8 \times 10^6$ cfu/ml | $3.5 \times 10^6$ cfu/ml |
| P. aeruginosa 9027 | $4.0 \times 10^6$ cfu/mml | $3.2 \times 10^6$ cfu/ml |
| B. cepacia 25416 | $3.0 \times 10^6$ cfu/ml | $1.8 \times 10^6$ cfu/ml |
| C. albicans 10231 | $2.7 \times 10^6$ cfu/ml | $1.7 \times 10^6$ cfu/ml |
| A. niger 16404 | $1.3 \times 10^6$ cfu/ml | $4.9 \times 10^5$ cfu/ml |

| | | ASSAY INTERVALS | | | |
|---|---|---|---|---|---|
| TEST ORGANISMS | 48 HRS | 7 D | 14 D | 21 D | 28 D |
| USE LEVEL: 0.3% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 5.8E3 | 2E1 | <10 | <10 | <10 |
| A. niger 16404 | 1.8E2 | <10 | <10 | <10 | <10 |
| USE LEVEL: 0.4% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

EXAMPLE 9

ANTIMICROBIAL: 1,2-Octanediol/Phenoxyethanol (40/60)/1.5% BIT

PRODUCT BASE: Nonionic Emulsion

| TEST ORGANISMS | INOCULUM (0 hours) | REINOCULUM (21 days) |
|---|---|---|
| Staph aureus 6538 | $3.0 \times 10^6$ cfu/ml | $2.8 \times 10^6$ cfu/ml |
| E. coli 8739 | $5.8 \times 10^6$ cfu/ml | $3.5 \times 10^6$ cfu/ml |
| P. aeruginosa 9027 | $4.0 \times 10^6$ cfu/ml | $3.2 \times 10^6$ cfu/ml |
| B. cepacia 25416 | $3.0 \times 10^6$ cfu/ml | $1.8 \times 10^6$ cfu/ml |
| C. albicans 10231 | $2.7 \times 10^6$ cfu/ml | $1.7 \times 10^6$ cfu/ml |
| A. niger 16404 | $1.3 \times 10^6$ cfu/ml | $4.9 \times 10^5$ cfu/ml |

| | | ASSAY INTERVALS | | | |
|---|---|---|---|---|---|
| TEST ORGANISMS | 48 HRS | 7 D | 14 D | 21 D | 28 D |
| USE LEVEL: 0.50% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 8E1 | <10 | <10 | <10 | <10 |
| USE LEVEL: 0.67% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

EXAMPLE 10

ANTIMICROBIAL: 1,2-Octanediol/Phenoxyethanol (40/60)/2.5% BIT

PRODUCT BASE: Nonionic Emulsion

| TEST ORGANISMS | INOCULUM (0 hours) | REINOCULUM (21 days) |
|---|---|---|
| Staph aureus 6538 | $3.0 \times 10^6$ cfu/ml | $2.8 \times 10^6$ cfu/ml |
| E. coli 8739 | $5.8 \times 10^6$ cfu/ml | $3.5 \times 10^6$ cfu/ml |
| P. aeruginosa 9027 | $4.0 \times 10^6$ cfu/ml | $3.2 \times 10^6$ cfu/ml |
| B. cepacia 25416 | $3.0 \times 10^6$ cfu/ml | $1.8 \times 10^6$ cfu/ml |
| C. albicans 10231 | $2.7 \times 10^6$ cfu/ml | $1.7 \times 10^6$ cfu/ml |
| A. niger 16404 | $1.3 \times 10^6$ cfu/ml | $4.9 \times 10^5$ cfu/ml |

| | | ASSAY INTERVALS | | | |
|---|---|---|---|---|---|
| TEST ORGANISMS | 48 HRS | 7 D | 14 D | 21 D | 28 D |
| USE LEVEL: 0.30% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 1E4 | 8.6E2 | 2.1E2 | 3E1 | 8.3E2 |
| USE LEVEL: 0.40% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 1E1 | <10 | <10 | <10 | <10 |

EXAMPLE 11

ANTIMICROBIAL: 1,2-Octanediol/Phenoxyethanol (40/60), 6% Sorbic Acid

PRODUCT BASE: Nonionic Emulsion

| TEST ORGANISMS | INOCULUM (0 hours) | REINOCULUM (21 days) |
|---|---|---|
| Staph aureus 6538 | $1.3 \times 10^6$ cfu/ml | $8.0 \times 10^6$ cfu/ml |
| E. coli 8739 | $3.9 \times 10^6$ cfu/ml | $4.8 \times 10^6$ cfu/ml |

-continued

| | | |
|---|---|---|
| P. aeruginosa 9027 | $2.5 \times 10^6$ cfu/ml | $4.7 \times 10^6$ cfu/ml |
| B. cepacia 25416 | $1.5 \times 10^6$ cfu/ml | $1.0 \times 10^6$ cfu/ml |
| C. albicans 10231 | $3.2 \times 10^6$ cfu/ml | $1.6 \times 10^6$ cfu/ml |
| A. niger 16404 | $4.0 \times 10^5$ cfu/ml | $2.6 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.5% | | | | | |
| Staph. aureus 6538 | 1.1E2 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | 8E3 | 7E4 | 1.1E5 |
| C. albicans 10231 | >1E6 | 3.1E4 | <10 | <10 | >1E4 |
| A. niger 16404 | 8.3E5 | 4E1 | <10 | <10 | 1E1 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 1.2E4 | <10 | <10 | <10 | <10 |
| A. niger 16404 | 3E5 | <10 | <10 | <10 | <10 |

EXAMPLE 12

ANTIMICROBIAL: 1,2-Octanediol/Phenoxyethanol (40/60), 6% sorbic acid

PRODUCT BASE: Nonionic Emulsion

| TEST ORGANISMS | INOCULUM (0 hours) | REINOCULUM (21 days) |
|---|---|---|
| Staph aureus 6538 | $6.9 \times 10^6$ cfu/ml | $1.8 \times 10^6$ cfu/ml |
| E. coli 8739 | $7.8 \times 10^6$ cfu/ml | $3.5 \times 10^6$ cfu/ml |
| P. aeruginosa 9027 | $5.1 \times 10^6$ cfu/ml | $1.3 \times 10^6$ cfu/ml |
| B. cepacia 25416 | $2.2 \times 10^6$ cfu/ml | $7.0 \times 10^6$ cfu/ml |
| C. albicans 10231 | $3.7 \times 10^6$ cfu/ml | $6.0 \times 10^7$ cfu/ml |
| A. niger 16404 | $1.8 \times 10^5$ cfu/ml | $8.0 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.50% | | | | | |
| Staph. aureus 6538 | 1E1 | <10 | <10 | <10 | <10 |
| E. coli 8739 | 6E1 | <10 | <10 | <10 | <10 |
| P. aeruginosa 9027 | 1E2 | <10 | <10 | <10 | <10 |
| B. cepacia 25416 | 5.8E4 | <10 | <10 | <10 | <10 |
| C. albicans 10231 | >1E6 | 1.7E5 | 2E1 | <10 | >1E4 |
| A. niger 16404 | 1E5 | 5.8E4 | 3E4 | 6E3 | 3.9E5 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 3E4 | <10 | <10 | <10 | <10 |

EXAMPLE 13

ANTIMICROBIAL: 1,2-Octanediol/Phenoxyethanol (40/60), 6% sorbic acid

PRODUCT BASE: Nonionic Emulsion

| TEST ORGANISMS | INOCULUM (0 hours) | REINOCULUM (21 days) |
|---|---|---|
| Staph aureus 6538 | $6.9 \times 10^6$ cfu/ml | $1.8 \times 10^6$ cfu/ml |
| E. coli 8739 | $7.8 \times 10^6$ cfu/ml | $3.5 \times 10^6$ cfu/ml |
| P. aeruginosa 9027 | $5.1 \times 10^6$ cfu/ml | $1.3 \times 10^6$ cfu/ml |
| B. cepacia 25416 | $2.2 \times 10^6$ cfu/ml | $7.0 \times 10^6$ cfu/ml |
| C. albicans 10231 | $3.7 \times 10^6$ cfu/ml | $6.0 \times 10^7$ cfu/ml |
| A. niger 16404 | $1.8 \times 10^5$ cfu/ml | $8.0 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.5% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | 8E1 | <10 | <10 | <10 | 2E1 |
| C. albicans 10231 | >1E6 | 1.4E4 | <10 | <10 | <10 |
| A. niger 16404 | 2.1E5 | 5.5E4 | 8E3 | 3E3 | 3.4E5 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 8E3 | <10 | <10 | <10 | <10 |

EXAMPLE 14

ANTIMICROBIAL: 1,2-Octanediol/Phenoxyethanol (40/60), 6% sorbic acid

PRODUCT BASE: Nonionic Emulsion

| TEST ORGANISMS | INOCULUM (0 hours) | REINOCULUM (21 days) |
|---|---|---|
| Staph aureus 6538 | $6.9 \times 10^6$ cfu/ml | $1.8 \times 10^6$ cfu/ml |
| E. coli 8739 | $7.8 \times 10^6$ cfu/ml | $3.5 \times 10^6$ cfu/ml |
| P. aeruginosa 9027 | $5.1 \times 10^6$ cfu/ml | $1.3 \times 10^6$ cfu/ml |
| B. cepacia 25416 | $2.2 \times 10^6$ cfu/ml | $7.0 \times 10^6$ cfu/ml |
| C. albicans 10231 | $3.7 \times 10^6$ cfu/ml | $6.0 \times 10^7$ cfu/ml |
| A. niger 16404 | $1.8 \times 10^5$ cfu/ml | $8.0 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.50% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | >1E6 | 2E4 | <10 | <10 | >1E4 |
| A. niger 16404 | 1.8E5 | 1.1E5 | 1.2E3 | 2E2 | >1E4 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |

-continued

| | | | | | |
|---|---|---|---|---|---|
| C. albicans 10231 | <10 | <10 | <10 | <10 | <10 |
| A. niger 16404 | 6E3 | <10 | <10 | <10 | 7E1 |

EXAMPLE 15

Antimicrobial: 1,2-Octanediol/Phenoxyethanol (40/60)
Product Base: Screening Emulsion

| TEST ORGANISMS | INOCULUM (0 hours) | REINOCULUM (21 days) |
|---|---|---|
| Staph aureus 6538 | $2.9 \times 10^6$ cfu/ml | $2.5 \times 10^5$ cfu/ml |
| E. coli 8739 | $4.7 \times 10^6$ cfu/ml | $3.4 \times 10^6$ cfu/ml |
| P. aeruginosa 9027 | $4.9 \times 10^6$ cfu/ml | $1.2 \times 10^6$ cfu/ml |
| B. cepacia 25416 | $5.3 \times 10^6$ cfu/ml | $1.1 \times 10^6$ cfu/ml |
| C. albicans 10231 | $1.0 \times 10^6$ cfu/ml | $1.1 \times 10^6$ cfu/ml |
| A. niger 16404 | $7.0 \times 10^5$ cfu/ml | $4.4 \times 10^5$ cfu/ml |

| | ASSAY INTERVALS | | | | |
|---|---|---|---|---|---|
| TEST ORGANISMS | 48 HRS | 7 D | 14 D | 21 D | 28 D |
| USE LEVEL: 0.5% | | | | | |
| Staph. aureus 6538 | 7E1 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 4E4 | <10 | <10 | <10 | 1E1 |
| A. niger 16404 | 2.3E5 | 2.3E4 | 2.5E2 | 2E1 | >1E4 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 3E4 | <10 | <10 | <10 | <10 |

EXAMPLE 16

ANTIMICROBIAL: 20 Pentanediol/20 Hexanediol/20 Octanediol/40 Phenoxyethanol
PRODUCT BASE: Screening Emulsion

| TEST ORGANISMS | INOCULUM (0 hours) | REINOCULUM (21 days) |
|---|---|---|
| Staph aureus 6538 | $2.5 \times 10^6$ cfu/ml | $2.5 \times 10^6$ cfu/ml |
| E. coli 8739 | $6.0 \times 10^6$ cfu/ml | $2.9 \times 10^6$ cfu/ml |
| P. aeruginosa 9027 | $5.7 \times 10^6$ cfu/ml | $2.3 \times 10^6$ cfu/ml |
| B. cepacia 25416 | $3.4 \times 10^6$ cfu/ml | $1.5 \times 10^6$ cfu/ml |
| C. albicans 10231 | $2.9 \times 10^6$ cfu/ml | $1.1 \times 10^6$ cfu/mkl |
| A. niger 16404 | $5.1 \times 10^5$ cfu/ml | $2.8 \times 10^5$ cfu/ml |

| | ASSAY INTERVALS | | | | |
|---|---|---|---|---|---|
| TEST ORGANISMS | 48 HRS | 7 D | 14 D | 21 D | 28 D |
| USE LEVEL: 0.25% | | | | | |
| Staph. aureus 6538 | 1.1E6 | 1.6E3 | <10 | <10 | >1E4 |
| E. coli 8739 | 2E2 | <10 | <10 | <10 | <10 |
| P. aeruginosa 9027 | 3E1 | 3E3 | 4E1 | 1E2 | >1E4 |
| B. cepacia 25416 | >1E6 | >1E6 | 4.3E5 | 1.8E5 | >1E6 |
| C. albicans 10231 | 7.9E5 | 1.2E5 | 4.1E2 | 2.2E2 | >1E4 |
| A. niger 16404 | 1.8E5 | 3.2E5 | 3.3E5 | 1.4E5 | 5.1E5 |
| USE LEVEL: 0.50% | | | | | |
| Staph. aureus 6538 | 9.8E4 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | 2.7E5 | <10 | <10 | <10 | <10 |
| C. albicans 10231 | 3.8E5 | 2E2 | <10 | <10 | 8E1 |
| A. niger 16404 | 2.6E5 | 3.3E5 | 1.7E3 | 8E2 | >1E4 |

EXAMPLE 17

ANTIMICROBIAL: 20 Pentanediol/20 Hexanediol/20 Octanediol/40 Phenoxyethanol
PRODUCT BASE: Nonionic Emulsion

| TEST ORGANISMS | INOCULUM (0 hours) | REINOCULUM (21 days) |
|---|---|---|
| Staph aureus 6538 | $2.5 \times 10^6$ cfu/ml | $2.5 \times 10^6$ cfu/ml |
| E. coli 8739 | $6.0 \times 10^6$ cfu/ml | $2.9 \times 10^6$ cfu/ml |
| P. aeruginosa 9027 | $5.7 \times 10^6$ cfu/ml | $2.3 \times 10^6$ cfu/ml |
| B. cepacia 25416 | $3.4 \times 10^6$ cfu/ml | $1.5 \times 10^6$ cfu/ml |
| C. albicans 10231 | $2.9 \times 10^6$ cfu/ml | $1.1 \times 10^6$ cfu/mkl |
| A. niger 16404 | $5.1 \times 10^5$ cfu/ml | $2.8 \times 10^5$ cfu/ml |

| | ASSAY INTERVALS | | | | |
|---|---|---|---|---|---|
| TEST ORGANISMS | 48 HRS | 7 D | 14 D | 21 D | 28 D |
| USE LEVEL: 0.5% | | | | | |
| Staph. aureus 6538 | 2.6E5 | <10 | <10 | <10 | <10 |
| E. coli 8739 | 2.2E4 | <10 | <10 | <10 | <10 |
| P. aeruginosa 9027 | <10 | <10 | <10 | <10 | <10 |
| B. cepacia 25416 | 2.6E5 | 6E3 | <10 | <10 | 2.9E3 |
| C. albicans 10231 | >1E6 | >1E6 | 4.8E4 | 7.1E2 | 9.3E5 |
| A. niger 16404 | 6.8E5 | 4.8E5 | 1.4E5 | >1E4 | 6.2E5 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | 1E2 | <10 | <10 | <10 | <10 |
| C. albicans 10231 | >1E6 | 2.8E4 | <10 | <10 | <10 |
| A. niger 16404 | 3.8E5 | 3.5E5 | 1.3E4 | 2.9E2 | 5.3E4 |

EXAMPLE 18

ANTIMICROBIAL: 20 Pentanediol/20 Hexanediol/20 Octanediol/40 Phenoxyethanol
PRODUCT BASE: Screening Emulsion

| TEST ORGANISMS | INOCULUM (0 hours) | REINOCULUM (21 days) |
|---|---|---|
| Staph aureus 6538 | $1.8 \times 10^6$ cfu/ml | $1.0 \times 10^6$ cfu/ml |
| E. coli 8739 | $3.5 \times 10^6$ cfu/ml | $3.6 \times 10^6$ cfu/ml |
| P. aeruginosa 9027 | $1.3 \times 10^6$ cfu/ml | $2.9 \times 10^6$ cfu/ml |
| B. cepacia 25416 | $7.0 \times 10^6$ cfu/ml | $3.0 \times 10^6$ cfu/ml |

-continued

| | | |
|---|---|---|
| C. albicans 10231 | $6.0 \times 10^5$ cfu/ml | $2.1 \times 10^6$ cfu/ml |
| A. niger 16404 | $8.0 \times 10^5$ cfu/ml | $2.8 \times 10^5$ cfu/ml |

| | ASSAY INTERVALS | | | | |
|---|---|---|---|---|---|
| TEST ORGANISMS | 48 HRS | 7 D | 14 D | 21 D | 28 D |
| USE LEVEL: 0.5% | | | | | |
| Staph. aureus 6538 | 1.3E4 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 2 5416 | 1.9E5 | <10 | <10 | <10 | <10 |
| C. albicans 10231 | 3E5 | 3.3E3 | <10 | <10 | 9.7E2 |
| A. niger 16404 | 6.8E5 | 6E4 | 3.3E4 | 1.1E4 | 6E4 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 3.8E2 | <10 | <10 | <10 | <10 |
| A. niger 16404 | 4.9E4 | 1.4E4 | 1.7E2 | 1.3E2 | 6.7E3 |

EXAMPLE 19

ANTIMICROBIAL: 1,2-Octanediol/Phenoxyethanol (40/60), 1.25% IPBC
PRODUCT BASE: Screening Emulsion

| TEST ORGANISMS | INOCULUM (0 hours) | REINOCULUM (21 days) |
|---|---|---|
| Staph aureus 6538 | $3.6 \times 10^6$ cfu/ml | $1.6 \times 10^6$ cfu/ml |
| E. coli 8739 | $4.0 \times 10^6$ cfu/ml | $2.2 \times 10^6$ cfu/ml |
| P. aeruginosa 9027 | $4.4 \times 10^6$ cfu/ml | $1.7 \times 10^6$ cfu/ml |
| B. cepacia 25416 | $3.0 \times 10^6$ cfu/ml | $1.7 \times 10^6$ cfu/ml |
| C. albicans 10231 | $4.2 \times 10^6$ cfu/ml | $9.3 \times 10^5$ cfu/ml |
| A. niger 16404 | $9.0 \times 10^5$ cfu/ml | $2.6 \times 10^5$ cfu/ml |

| | ASSAY INTERVALS | | | | |
|---|---|---|---|---|---|
| TEST ORGANISMS | 48 HRS | 7 D | 14 D | 21 D | 28 D |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |
| USE LEVEL: 1.8% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

What is claimed is:

1. An antimicrobial composition consisting essentially of, by weight, based on the total weight of (a) and (b):
    (a) 40-60% of a mixture of 1,2-pentanediol, 1,2-hexanediol and 1,2-octanediol;
    (b) 40-60% phenoxyethanol; and
    (c) a co-biocide present in an amount us to 10% said co-biocide selected from the group consisting of sorbic acid, benzoic acid, dibromodicyano-butane, 1,2-benzisothiazolin-3-one, and mixtures thereof, wherein said antimicrobial composition is active against at least one of E. coli, Staph aureus, P. aeruginosa, B. cepacia, C. albicans, and A. niger.

2. An antimicrobial composition in accordance with claim 1 wherein (a) comprises equal parts 1,2-pentanediol, 1,2-hexanediol and 1,2-octanediol.

3. An antimicrobial composition in accordance with claim 1 wherein the co-biocide is sorbic acid or 1,2-benzisothiazolin-3-one.

4. An antimicrobial composition in accordance with claim 3 wherein the co-biocide comprises sorbic acid present in an amount of about 5-7%.

5. An antimicrobial composition in accordance with claim 1 wherein the composition comprises 41-42% (a) and 52-53% (b).

6. An antimicrobial composition in accordance with claim 5 wherein the co-biocide comprises sorbic acid present in an amount of about 5-7%.

* * * * *